(12) United States Patent
Walkenhorst et al.

(10) Patent No.: US 9,237,908 B2
(45) Date of Patent: Jan. 19, 2016

(54) DYNAMIC STABILIZATION SYSTEM FOR THE SPINE

(75) Inventors: Jared W. Walkenhorst, Fairfield, CT (US); Michael E. Landry, Austin, TX (US); Thomas G. Wilson, Guilford, CT (US); John A. Pafford, Eads, TN (US)

(73) Assignee: Spine Wave, Inc., Shelton, CT (US)

( * ) Notice: Subject to any disclaimer, the term of this patent is extended or adjusted under 35 U.S.C. 154(b) by 2829 days.

(21) Appl. No.: 11/408,725

(22) Filed: Apr. 21, 2006

(65) Prior Publication Data

US 2006/0293663 A1    Dec. 28, 2006

Related U.S. Application Data

(60) Provisional application No. 60/673,646, filed on Apr. 21, 2005.

(51) Int. Cl.
*A61B 17/70* (2006.01)
*A61B 17/84* (2006.01)
*A61B 17/88* (2006.01)
*A61B 17/90* (2006.01)

(52) U.S. Cl.
CPC ......... *A61B 17/7067* (2013.01); *A61B 17/7064* (2013.01); *A61B 17/7055* (2013.01); *A61B 17/842* (2013.01); *A61B 17/8875* (2013.01); *A61B 2017/90* (2013.01)

(58) Field of Classification Search
CPC ............ A61B 17/7064; A61B 17/7062; A61F 2/4405
USPC ........................................................ 606/247
See application file for complete search history.

(56) References Cited

U.S. PATENT DOCUMENTS

| 2,677,369 | A |   | 5/1954  | Knowles |
|-----------|---|---|---------|---------|
| 4,309,777 | A |   | 1/1982  | Patil |
| 4,865,604 | A | * | 9/1989  | Rogozinski ................ 623/23.42 |
| 5,011,484 | A |   | 4/1991  | Bréard |
| 5,496,318 | A |   | 3/1996  | Howland et al. |
| 5,569,248 | A |   | 10/1996 | Mathews |
| 5,609,634 | A |   | 3/1997  | Voydeville |
| 5,645,599 | A |   | 7/1997  | Samani |
| 5,791,899 | A |   | 8/1998  | Sachdeva et al. |
| 5,860,977 | A |   | 1/1999  | Zucherman et al. |
| 6,158,437 | A | * | 12/2000 | Vagley .......................... 128/898 |
| 6,440,169 | B1 |  | 8/2002  | Elberg et al. |
| 6,579,319 | B2 | * | 6/2003  | Goble et al. ................ 623/17.11 |
| 6,607,530 | B1 |  | 8/2003  | Carl et al. |

(Continued)

FOREIGN PATENT DOCUMENTS

WO    WO 03057054 A2 *  7/2003 ............. A61B 17/58

*Primary Examiner* — Eduardo C Robert
*Assistant Examiner* — Julianna N Harvey
(74) *Attorney, Agent, or Firm* — Hoffmann & Baron LLP

(57) ABSTRACT

A system for dynamic stabilization of the spine includes a bone engaging fastener configured to be anchored in a vertebra and a deflectable element mounted on the fastener. The deflectable element or bumper is configured and arranged to contact a portion of an adjacent vertebra, such as the facet, during extension of the spine, while offering no resistance during flexion. In certain embodiments, a cable may be fastened to the bone engaging fastener and arranged to contact a portion of the adjacent vertebra, such as the spinous process, during flexion of the spine. In one surgical technique of the invention, a contralateral approach is used to introduce the bone engaging fastener through the deflectable element and into the vertebra.

6 Claims, 17 Drawing Sheets

(56) References Cited

U.S. PATENT DOCUMENTS

| | | |
|---|---|---|
| 6,610,091 B1 * | 8/2003 | Reiley .................. 606/247 |
| 6,626,905 B1 | 9/2003 | Schmiel et al. |
| 6,626,944 B1 | 9/2003 | Taylor |
| 6,733,534 B2 | 5/2004 | Sherman |
| 6,875,212 B2 | 4/2005 | Shaolian et al. |
| 6,966,930 B2 * | 11/2005 | Arnin et al. ........... 623/17.11 |
| 6,986,771 B2 | 1/2006 | Paul et al. |
| 2004/0034353 A1 | 2/2004 | Michelson |
| 2004/0044347 A1 * | 3/2004 | Cassell ................. 606/92 |
| 2004/0097927 A1 | 5/2004 | Yeung et al. |
| 2004/0172019 A1 * | 9/2004 | Ferree ................. 606/61 |
| 2005/0033434 A1 * | 2/2005 | Berry ................. 623/17.14 |
| 2005/0070899 A1 * | 3/2005 | Doubler et al. ......... 606/61 |
| 2005/0131405 A1 * | 6/2005 | Molz et al. ........... 606/61 |
| 2005/0154390 A1 | 7/2005 | Biedermann et al. |
| 2005/0288672 A1 * | 12/2005 | Ferree ................. 606/61 |
| 2006/0122609 A1 * | 6/2006 | Mirkovic et al. ........ 606/72 |
| 2006/0122610 A1 | 6/2006 | Culbert et al. |

* cited by examiner

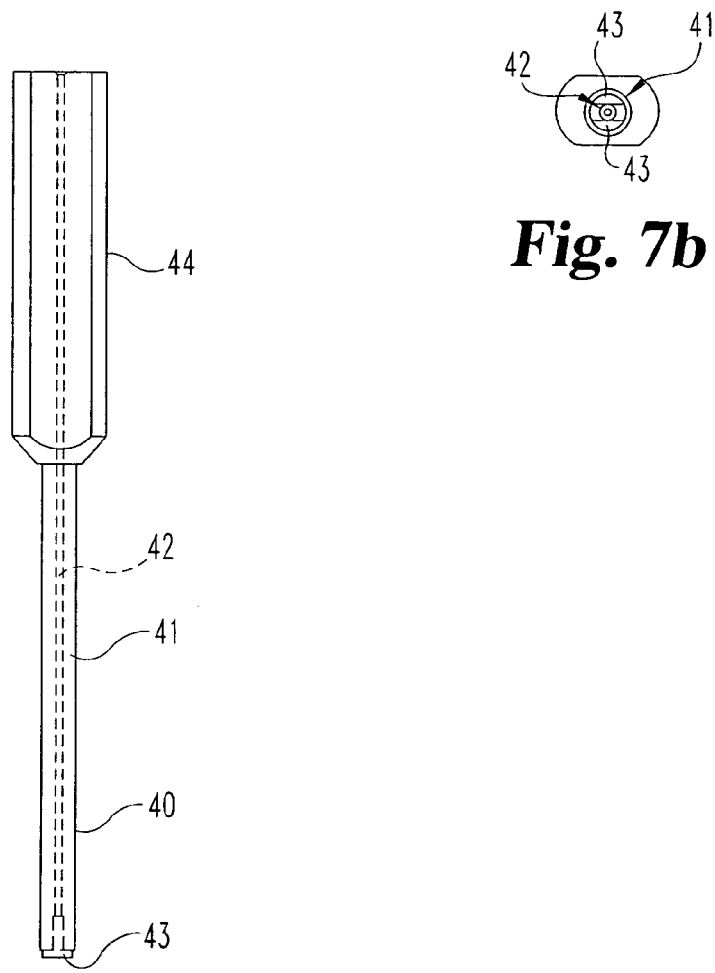
Fig. 7b
Fig. 7a
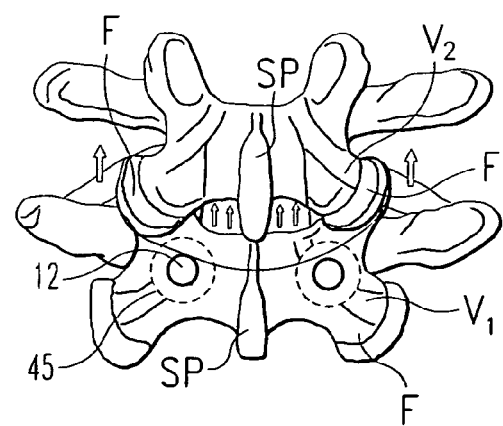
Fig. 8

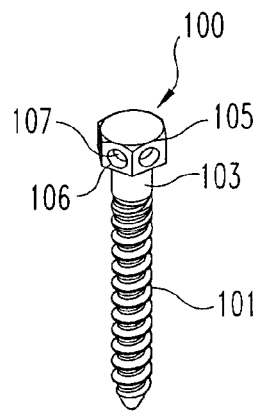
*Fig. 16a*
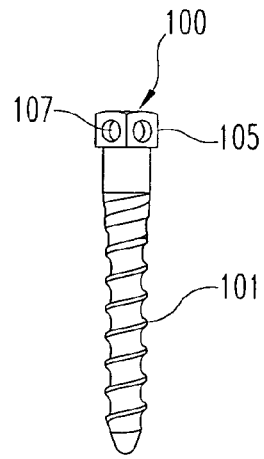
*Fig. 16b*
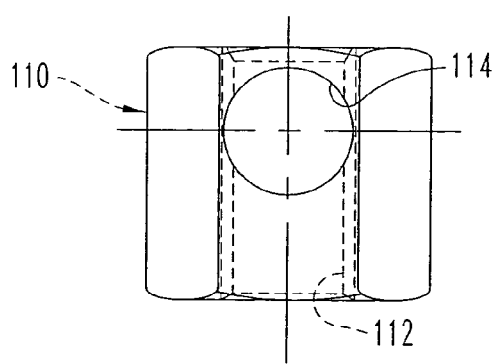
*Fig. 17a*     *Fig. 17b*
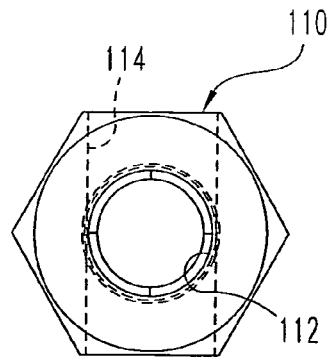
*Fig. 17c*

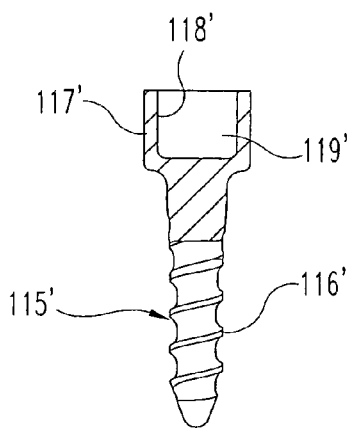
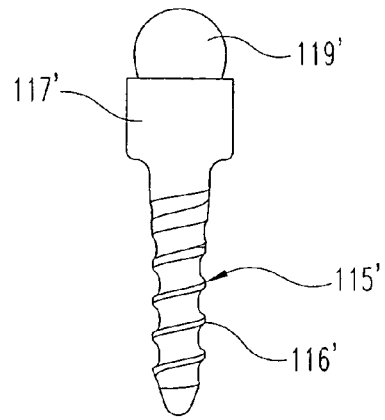
*Fig. 22a*    *Fig. 22b*
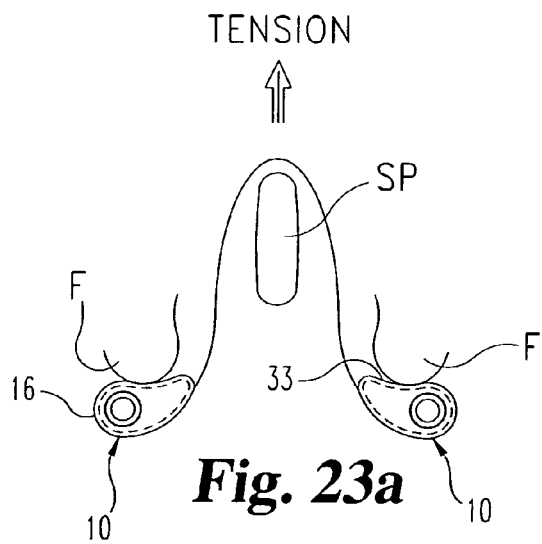
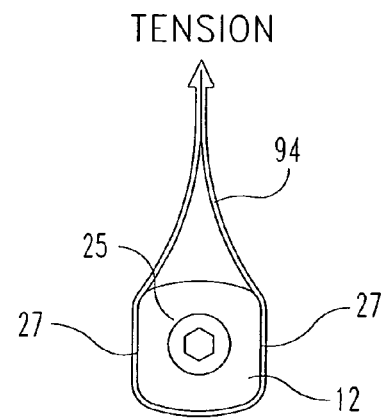
*Fig. 23a*    *Fig. 23b*

DYNAMIC STABILIZATION SYSTEM FOR THE SPINE

REFERENCE TO RELATE APPLICATION

The present application claims priority to provisional application No. 60/673,646, filed on Apr. 21, 2005 and entitled "Interspinous Dynamic Stabilization System", the entire disclosure of which is incorporated herein by reference.

BACKGROUND OF THE INVENTION

The present invention relates to spinal implants and stabilization systems. More particularly, the invention concerns a dynamic stabilization system that is disposed in between adjacent vertebrae.

In the past, the principal protocol for the treatment of the spine has been rigid fixation combined with fusion of the affected vertebral body or intervertebral disc. Arthrodesis, as this approach is known, has been achieved with a variety of rigid fixation elements, such as spinal rods or plates that are rigidly fixed to a vertebra using bone screws, bone bolts and spinal hooks. However, spinal fusion has been recognized to have limitations in the treatment of disc degeneration, especially in the earlier stages of the degeneration where it may be unnecessary to eliminate motion of the spinal motion segments.

Clinical studies suggest that cells of the intervertebral disc respond favorably to reduced (but not eliminated) mechanical loading through deposition of extracellular matrix proteins (collagen, proteoglycan, fibronectin, etc.) into the disc space. In some cases, a degenerated disc may simply involve a mechanically overloaded and hypermobile segment that can be repaired by reversing the mechanically damaging load environment. For instance, clinical experiences with dynamic stabilization systems suggest that the disc becomes increasingly hydrated over time, as judged by MRI scanning.

Spinal instability is a recognized effect of degenerative disc disease. In contrast to arthrodesis, arthroplasty is a protocol that contemplates restoring segmental spinal motion while treating the degenerative condition. Arthroplasty has been successfully used in the treatment of degenerative conditions of the hip and knee. In recent years, efforts have been made to implement arthroplasty in the spine, and most particularly in the intervertebral space. Intradiscal arthroplasty is now clinically available in the form of articulating prosthetic discs and polymeric disc nucleus replacements. With the availability of viable intradiscal arthroplasty devices, interest has grown in providing some means for dynamic spinal stabilization—i.e., stabilization that still permits some degree of mobility between spinal segments.

Drawing from the approaches developed for intradiscal arthroplasty, efforts have made to develop an extradiscal arthroplasty. These systems offer the advantage of "soft stabilization" that limit, rather than eliminate, spinal segment motion. Current theories suggest that preventing movement of the spinal segments may not be a significant factor in clinical success of spinal stabilization systems. Instead, these theories focus on creating a normal loading pattern for the spine as a primary vehicle for successful spinal instrumentation. Thus, the goals for dynamic stabilization has been to restrict movement of the spine to a zone or range where normal or near normal loading of the spinal segments can occur. At the same time, dynamic stabilization techniques have sought to prevent the spine from adopting a position or orientation where abnormal loading of the spine can occur. An acceptable outcome of dynamic stabilization is to make the instrumented spinal level more flexible than rigid (which would occur with fusion), but less flexible than normal.

One approach to achieve these goals for dynamic stabilization utilizes the spinous process. Thus, in one system, flexible "ligament" are engaged around the spinous process of adjacent vertebrae. Another form of flexible "ligament" is attached to the spinous process by way of small screws. In yet another approach, a polymeric spacer is held in place between the adjacent spinous processes. One system utilizes a coil spring that spans several vertebrae and that is anchored to the lamina of the end vertebrae. In one version, a rod extends through part of the coil spring to control rotation.

A similar construct employs a bearing cushion fixed between the spinous processes of adjacent vertebrae, as depicted in FIG. 1. This cushion 1 includes a U-shaped member having opposite brackets 2 for engagement to the spinous processes SP and separated by a flexible central portion 3. In certain embodiments, a cushion element 4 is disposed between the brackets 2 to limit the movement of the brackets, and therefore the adjacent vertebrae, towards each other. Details of this bearing cushion can be discerned from U.S. Pat. No. 5,645,599, the disclosure of which is incorporated by reference herein. As with the ligament-type systems, this bearing cushion resists movement of the adjacent vertebrae in flexion as well as extension. The addition of the cushion element increases the resistance in extension.

In another approach, resistance to flexion is eliminated, with the damping effect experienced only during extension. In this system, an insert 5 is held to the spinous process of a vertebra by a band or cable 7 encircling the spinous process. The insert 5 includes lips or wings 6 that contact each other when the anterior aspect of the vertebrae move together in extension. Details of this system are found in U.S. Pat. No. 5,011,484, the disclosure of which is incorporated herein by reference.

Some dynamic stabilization systems have relied upon fixation to the pedicle of the vertebrae. In these types of systems, a pedicle screw is threaded into the pedicle of adjacent vertebrae. A member spans between the heads of the pedicle screws to limit the movement of the spinal segments. In one device, known as the Graf Ligament, a non-elastic band is wrapped around pedicle screw anchors. The non-elastic bands lock the spinal segment into lordosis, while permitting minimal rotation movements of the spine.

Another system utilizing pedicle screws, provided by Zimmer, Inc. as the Dynesys System, incorporates a polymeric cylinder between the bone anchors. The Dynesys System permits, but limits, relative motion between adjacent vertebrae. An apparatus known as the FASS System essentially integrates features from the Graf and Dynesys systems.

The DSS System employs still another approach by including a spring element connected to pedicle screws. The spring element is contained within a polyurethane tube to prevent tissue ingrowth. Finally, some systems utilize a rigid member, such as a spinal plate, spanning between vertebrae. The flexible stabilization feature is incorporated into the interface between the pedicle screw and the rigid member, such as through a flexible washer or a spherical screw-plate interface.

There remains a need for a dynamic stabilization system that efficiently permits dynamic movement of the spinal motion segments while restricting the range of this movement.

SUMMARY OF THE INVENTION

In order to address this need, one embodiment of the invention provides a dynamic stabilization system for the spine comprising a bone engaging fastener configured to be anchored in a vertebra and a deflectable element, or bumper element, mounted on the fastener. The deflectable element is configured and arranged to contact a portion of an adjacent vertebra during extension of the spine when the fastener is engaged within a vertebra. In certain embodiments, the deflectable element is a resiliently deformable, while other embodiments rely upon mechanical deflection. The deflectable element resists movement of the adjacent vertebrae toward each other in extension but offers no resistance to movement of the vertebrae apart during flexion.

In one aspect, the dynamic stabilization system may be implanted while the spine of the patient is in flexion, thereby widening the space between the posterior aspects of the adjacent vertebrae. With the spine in flexion, the stabilization system may be readily implanted into one vertebra so that when the flexion is removed the adjacent vertebra will contact the deflectable element. In this way, the deflectable element may provide a certain amount of posterior distraction of the adjacent vertebrae. In some embodiments, the deflectable element is configured with an angled surface that can bear against the adjacent vertebra as the deflectable element is mounted on the bone engaging fastener. With these embodiments, the implantation of the deflectable element itself will distract the adjacent vertebrae and the element will maintain this distraction when the construct is complete.

The bone engaging fastener may include a shank having bone engaging threads, a threaded stem and a nut configured for engaging the threaded stem. In this embodiment, the deflectable element defines an opening to receive the threaded stem therethrough. The nut then bears on the deflectable element to mount the deflectable element on the fastener. Where the deflectable element is resiliently deformable, the nut is used to compress the element so that the element deforms at the opening to firmly engage the stem of the bone engaging fastener to resist or prevent relative movement between the fastener and the deflectable element. In other embodiments, the threaded stem and the opening in the deflectable element are keyed to prevent relative rotation.

In one aspect of the invention, the bone engaging fastener includes a shoulder between the shank and the stem and the opening in the deflectable element is sized so that the deflectable element is compressed between a nut and the shoulder when the nut is threaded onto the stem of the fastener. In another aspect, the deflectable element is positioned in contact with the one vertebra while the bone engaging fastener is passed through the opening in the element and driven into the vertebra.

In certain embodiments, the deflectable element includes a spring element mounted to the bone engaging fastener. This spring element may include a wound leaf spring, a coil spring or two concentric coil springs. The spring element may also include an inner ring mounted to the bone engaging fastener, an outer ring configured to contact the adjacent vertebra, and a plurality of spring members connecting the outer ring to the inner ring.

In other embodiments, the deflectable element is an expandable element having a reduced first configuration and expandable to a larger second configuration for contacting the adjacent vertebra. The expandable element may include a balloon. The bone engaging fastener may include a head portion defining a cavity for receiving the balloon in its reduced first configuration.

In another aspect of the invention, a dynamic stabilization system for the spine comprises a pair of bone engaging fasteners configured to be anchored in a vertebra on opposite sides of the spinous process of the vertebra, and a deflectable element mounted on each fastener. The deflectable elements are configured and arranged to contact a portion of an adjacent vertebra during extension of the spine when the pair of fasteners are engaged within a vertebra. In certain embodiments, the system further comprises a cable connected at its ends to a corresponding one of the pair of bone engaging fasteners. The cable sized to engage a portion of the adjacent vertebra, such as the spinous process.

The present invention further contemplates a method for providing dynamic stabilization to the spine comprising providing a deflectable element having an opening therethrough, the deflectable element sized and configured to contact an adjacent vertebra when the deflectable element is mounted on a vertebra, positioning the deflectable element on the vertebra, and introducing a bone engaging fastener through the opening in the deflectable element and into the vertebra from a contralateral direction. The step of introducing the bone engaging fastener may include supporting a jig on the deflectable element, the jig including a fastener guide movable to variable angular orientations relative to the deflectable element, aligning the fastener guide to a desired angle relative to the vertebra, and passing the bone engaging fastener through the fastener guide to drive the fastener into the bone at the desired angle.

In another embodiment a method is offered for providing dynamic stabilization to the spine comprising anchoring a pair of bone engaging fasteners into a vertebra on opposite sides of the spinous process, and mounting a deflectable element to each of the bone engaging fasteners, each deflectable element sized and configured to contact an adjacent vertebra. In certain embodiments, prior to mounting the deflectable elements the spine in is placed flexion. The flexion is subsequently relieved so that the deflectable elements provide some distraction to the adjacent vertebrae. The method may further comprise connecting a cable to the pair of bone engaging fasteners with the cable arranged to contact the spinous process of the adjacent vertebra at least during flexion of the spine.

It is one object to provide a system and method for dynamic stabilization of the spine. It is a further object to provide a stabilization system that can be used to control the degree of motion of the spine in flexion and/or extension. Other objects and certain benefits of the present invention will be appreciated from the following written description and accompanying figures.

DESCRIPTION OF THE FIGURES

FIG. 4b is a side view of the bone anchor shown in FIG. 4a.

FIG. 7a is a side elevational view of a driving tool for implanting the bone anchor component of the dynamic stabilization system shown in FIGS. 3-5.

FIG. 7b is a bottom elevational view of the driving tool shown in FIG. 7a.

FIG. 8 is an enlarged view of adjacent vertebrae instrumented with a dynamic stabilization system in accordance with a further embodiment of the present invention.

FIG. 9b is a top elevational view of the bumper element shown in FIG. 9a.

FIG. 9c is a side elevational view of the bumper element shown in FIG. 9a.

FIG. 16a is a perspective view of a bone anchor that incorporates features for engaging a flexible cable in conjunction with supporting a bumper element in accordance with one embodiment of the invention.

FIG. 16b is a side view of the bone anchor shown in FIG. 16a.

FIG. 17a is side view of a nut for engaging a bone anchor such as the bolt shown in FIG. 4a or 9d that incorporates features for engaging a flexible cable.

FIG. 17b is a rotated side view of the nut depicted in FIG. 17a.

FIG. 17c is a top view of the nut shown in FIG. 17a.

FIG. 22a is a perspective view of an alternative dynamic stabilization system incorporating an expandable balloon element, with the element in its contracted configuration.

FIG. 22b is a perspective view of the dynamic stabilization system shown in FIG. 22a, with the balloon element in its expanded configuration.

FIG. 23a is a posterior view of an embodiment of the present invention in which a cable system is combined with a bumper element.

FIG. 23b is a posterior view of a cable system combined with a bone anchor of one embodiment of the invention.

FIG. 24b is a side view of the bumper element shown in FIG. 24a.

FIG. 25b is a top view of the bumper element illustrated in FIG. 25a.

FIG. 32b is a rotated side view of the bumper inserter tool shown in FIG. 32a.

DESCRIPTION OF THE PREFERRED EMBODIMENTS

Figure 1:
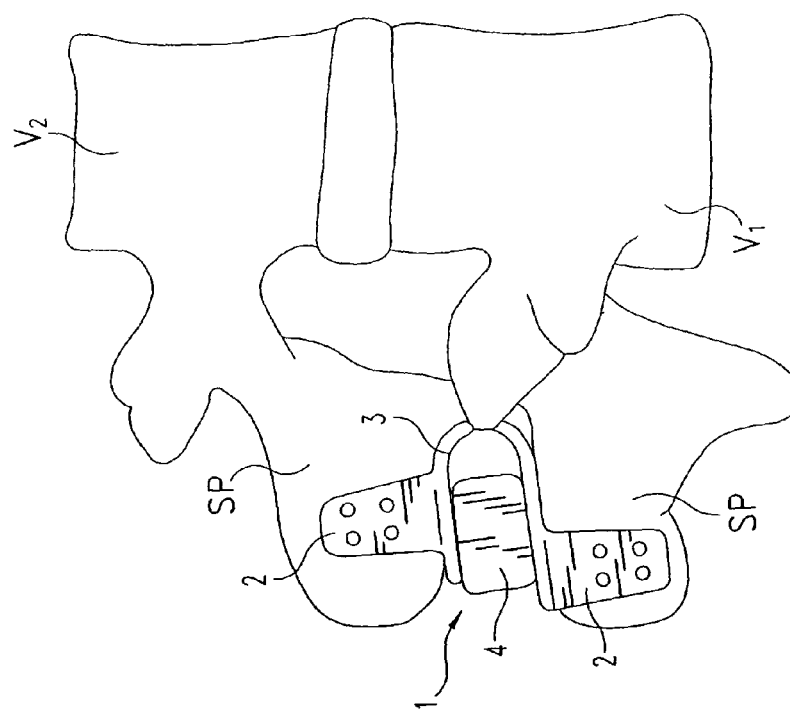
FIG. 1 is a lateral view of a bearing cushion of the prior art disposed between adjacent vertebrae.
Figure 2:
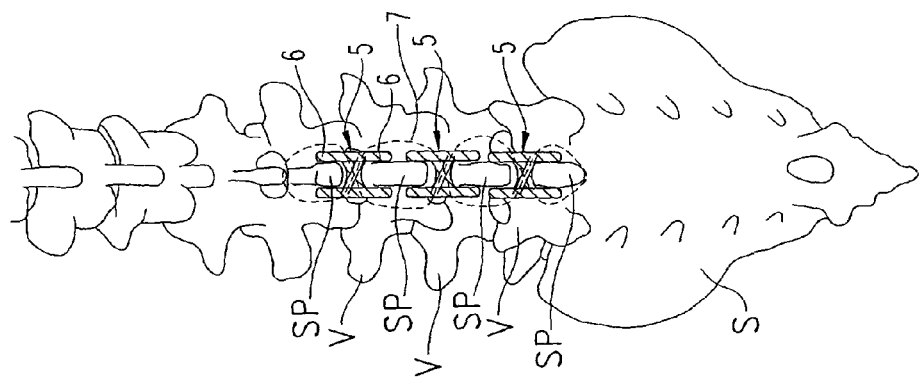
FIG. 2 is a posterior view of a portion of the spine instrumented with an insert system of the prior art disposed between vertebrae.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 3:
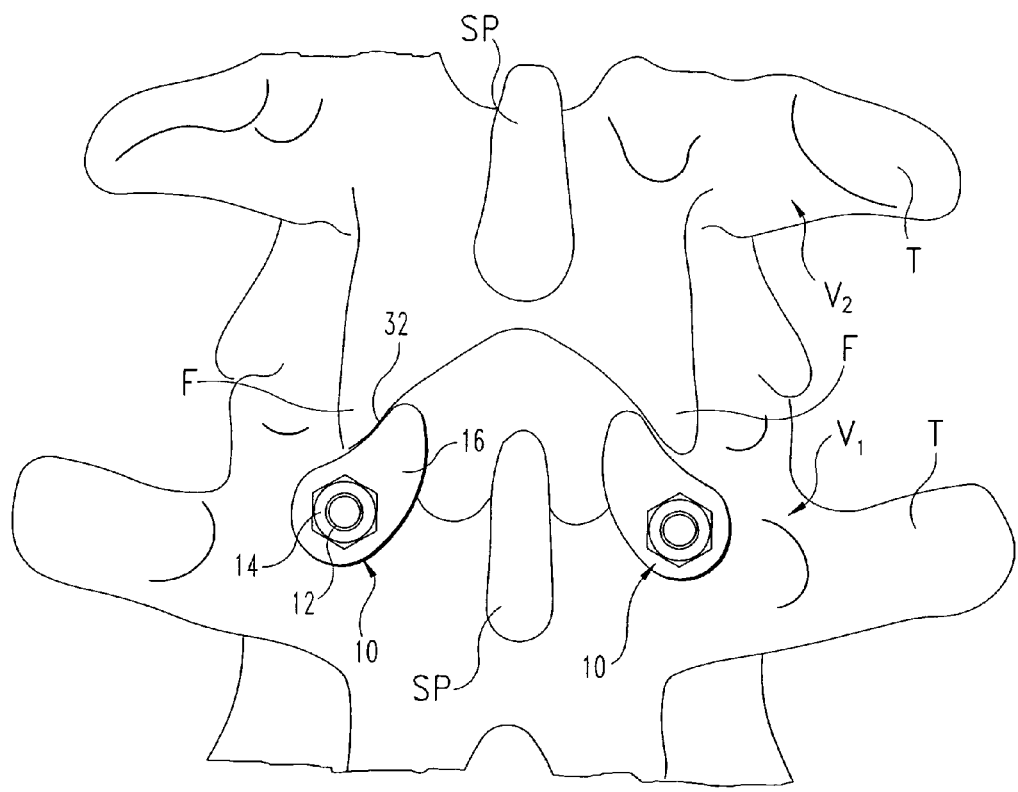
FIG. 3 is an enlarged view of a portion of adjacent vertebrae instrumented with a dynamic stabilization system in accordance with one embodiment of the present invention.
Figure 4B:
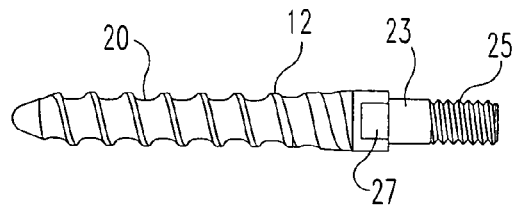
Figure 4A:
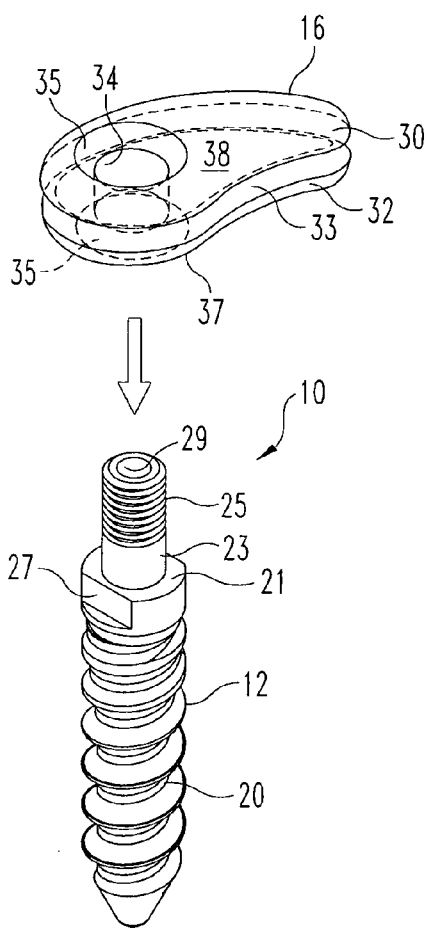
FIG. 4a is an enlarged exploded view of components of the dynamic stabilization system shown in FIG. 3.
Figure 5:
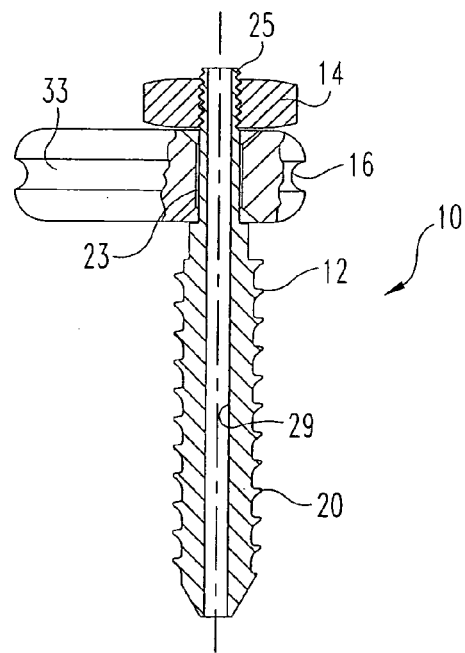
FIG. 5 is an enlarged partial cross-section view of the dynamic stabilization system shown in FIGS. 3 and 4.

Referring to FIGS. 3-6, a dynamic stabilization system 10 according to one embodiment of the invention is illustrated. As shown in FIG. 3, the system 10 includes a component engaged within one vertebra V1 and a component that bears against a portion of an adjacent vertebra V2. In particular, the system 10 includes a bone engaging fastener 12 that is configured to engage the body of the vertebra V1 and a bumper element 16 that is configured to bear against the facet F of the adjacent vertebra V2. The bumper element may be fixed to the bone engaging fastener 12 by a nut 14 or similar component, as illustrated in FIG. 5.

In this embodiment, the bone engaging fastener 12 is a bone anchor in the form of a bolt having a bone engaging portion 20, an intermediate shoulder portion 21 and a stem 23, as shown in FIGS. 4a, 4b and 5. The stem 23 is sized to pass through a bore 34 defined in the bumper element 16. The stem includes a threaded end 25 onto which the nut 14 is threaded to lock the bumper element 16 between the nut and the shoulder 21. The bone engaging portion 20 can include self-tapping threads. The bone anchor 12 may configured like bone anchors that may be used in conjunction with plate or rod systems forming spinal implant constructs.

Preferably the bone anchor 12 is cannulated with an inner cannula 29 to permit guide wire insertion of the bolt. The shoulder portion 21 can define driving flats 27 that are configured for engagement by the working end of a driving tool, such as the tool 40 shown in FIG. 7. The driving tool 40 may include a shaft terminating in a handle 44. The shaft is also cannulated 42 for use with a guide wire. The working end of the tool 40 includes a pair of wings 43 that are sized to engage the flats 27 to facilitate rotation of the bone anchor 12 as it is threaded into the vertebral body.

The body 30 of the bumper element 16 is formed of a flexible material, such as silicone or polyurethane, which can deflect slightly as the vertebrae move in extension. Importantly, the material of the bumper element is sufficiently rigid to be able to apply a constant distraction force between the adjacent vertebra V1 and V2. This constant distraction can be enough to induce a slight kyphosis to the instrumented motion segment. Maintaining this distraction helps reduce compression of the posterior segment and open the foramen and spinal canal, thereby significantly reducing the pain symptoms associated with deterioration of a motion segment.

Figure 6:
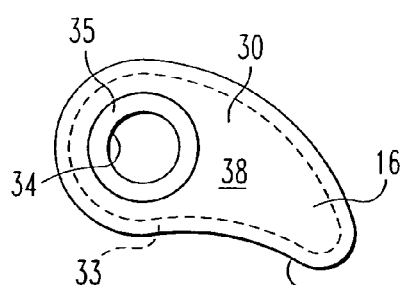
FIG. 6 is a top elevational view of a bumper element of the dynamic stabilization system shown in FIGS. 3-5.

The body 30 may include a contoured edge 32 between the bottom face 37 and top face 38. The edge bears against the adjacent vertebra V2 when the stabilizer 10 is implanted into the vertebra V1. In the preferred embodiment, the bumper element 16 bears against the facet F so the contoured edge 32 is shaped to generally conform to the surface of the facet. In addition, the contoured edge can be configured to create a camming effect, as best seen in FIG. 6, so that as the relative distance between the two vertebrae decreases the resistance of the bumper element increases. A groove 33 may be defined around the perimeter of the body 30. The bore 34 may terminate in a relief 35 at its opposite ends. As the nut 14 is tightened onto the bumper element 16 the body 30 is compressed and shoulder portion 21 of the bone anchor 12 may project into the relief 35 at the bottom face 37 of the body. As the body is compressed further between the nut and shoulder portion, the relief 35 conforms to the flats 27 to thereby fix the bumper element 16 in rotation relative to the bone anchor 12. As an alternative, the stem 23 and bore 34 can be complementary configured so that the bumper element can be moved to incremental angular positions—i.e., the stem and bore can have a male-female multi-sided configuration, such as a hex shape, to prevent relative rotation between the bumper element 16 and the bone anchor 12.

In accordance with this embodiment, the bone anchor 12 is threaded into an aspect of the vertebra V1, such as into the pedicle, in a known manner. With the bone anchor in position within the inferior vertebra, the bumper element 16 can be positioned on the stem 23 and oriented in contact with the facet F of the superior vertebra V2. Nominally, the patient is in the prone position with the spine in flexion to distract the adjacent vertebrae V1, V2. With the bumper element in its operative position, the nut 14 is tightened onto the threaded end 25 until the bumper element body 30 is solidly compressed between the nut and shoulder. As shown in FIG. 3, dynamic stabilizer systems 10 are preferably implanted on either side of the spinous process SP. It can be appreciated that the same bumper element 16 can be used on either side by simply flipping the element over.

The dynamic stabilization system 10 of the present invention is easily implanted using minimally invasive or working channel techniques. The same minimally invasive approaches used to implant a bone screw into a vertebral body can be implemented with the present invention. The envelope of the bumper element 16 is slightly larger than the profile of a bone bolt, so the working channel cannula or introducer cannula will be slightly larger than what is required for introduction of the bone anchor alone. However, it is contemplated that the bumper element 16 will not require a cannula that is larger than the working channels used to implant conventional fixation plates and the like in the spine.

Figure 9A:
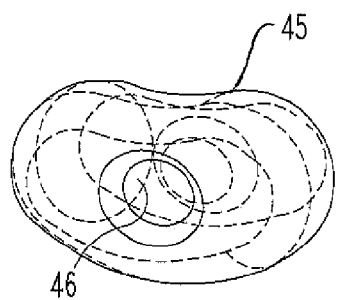
FIG. 9a is a top perspective view of a bumper element component of the dynamic stabilization system shown in FIG. 8.
Figure 9C:
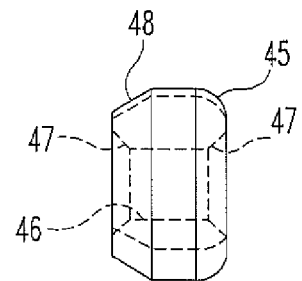
Figure 9B:
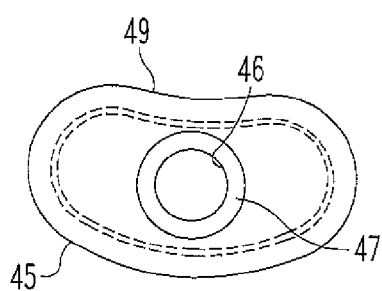

In an alternative approach, the dynamic stabilization system is itself used to distract the adjacent vertebrae. Thus, as shown in FIGS. 8-9, the bumper element 45 may be configured to apply a distraction force to the superior vertebra V2 as the bumper element is tightened onto the bone anchor 12 that is fixed within the inferior vertebra V1. In this embodiment of the invention, the bumper element 45 includes a bore 46 with a relief 47 at the opposite ends, like the bumper element 16 described above. The bumper element 45 may further include a tapered surface 48 (FIG. 9c) that bears against the facet of the superior vertebra as the bumper element is compressed onto the bone anchor. As can be seen in FIGS. 9a-9b, this bumper element 45 may have a kidney shape with a contoured surface 49 configured to bear against the adjacent vertebra. With this configuration, the bumper element 45 is preferably situated more centrally to the facet F, rather than toward the medial surface of the facet as with the bumper element 16.

Figure 9D:
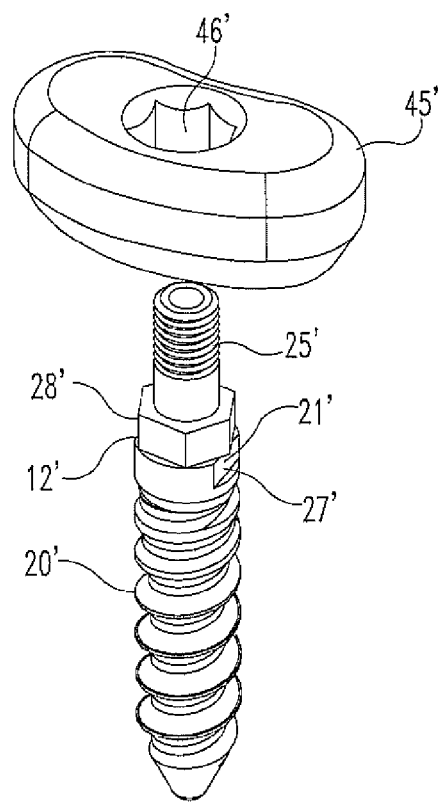
FIG. 9d is an exploded perspective view of a bumper element modified from the element shown in FIG. 9a and a bone anchor modified from the bolt shown in FIG. 4.

In a modification of the kidney-shaped bumper element, a bumper element 45' shown in FIG. 9d includes a bore 46' that incorporates an anti-rotation feature. In particular, the bore 46' is keyed or complementary to an anti-rotation feature 28' on a modified bone anchor 12'. The bone anchor 12' includes bone engaging threads 20', a shoulder 21', machine threads 25' and driving flats 27' similar to the like components on the bone anchor 12 of FIG. 4. However, with the bolt 12', the anti-rotation feature 28' is interposed between the driving flats 27' and the machine thread 25'. The feature 28' is complementary to the bore 46' so that once the bumper element 45' is mounted on the bolt it cannot rotate relative thereto.

Figure 10:
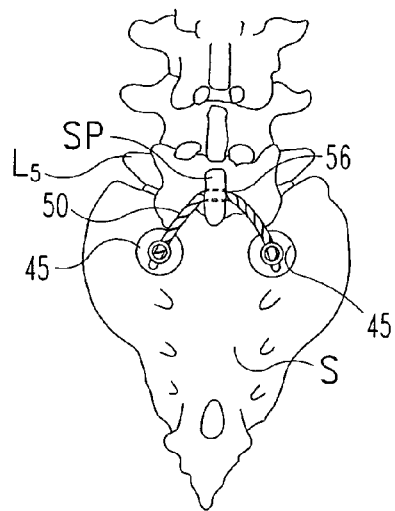
FIG. 10 is a posterior view of the L5 lumbar and sacral vertebrae instrumented with a dynamic stabilization system in accordance with another embodiment of the present invention.
Figure 11:
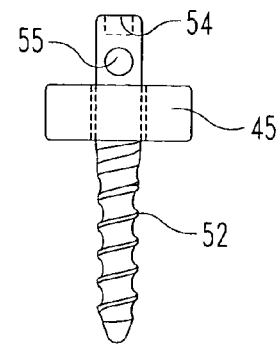
FIG. 11 is a side view of the dynamic stabilization system shown in FIG. 10.
Figure 12:
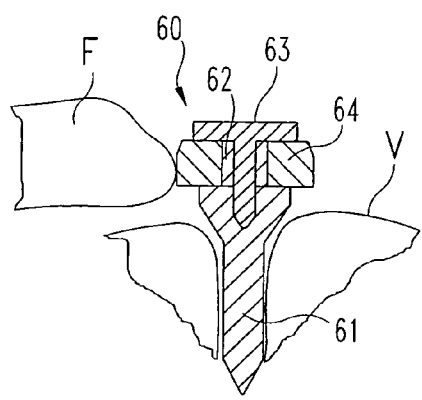
FIG. 12 is a side cross-sectional view of a dynamic stabilization system in accordance with an alternative embodiment of the invention.

The dynamic stabilization system of the present invention provides a significant advantage over prior dynamic systems, as best illustrated in FIG. 10. In particular, prior systems are not capable of providing dynamic stabilization at different motion segments along the length of the spine. Moreover, these prior systems are not capable of use at the lumbar-sacral motion segment. The dynamic stabilization system of this invention can be modified for fixation within the sacrum S (nominally the S1 vertebra) so that the bumper element, such as element 45, can bear against the facet of the lowermost lumbar vertebra L5. Thus, in this embodiment, a bone anchor 52 may be configured as a bone bolt, as shown in FIG. 11, for implantation within the sacrum S while supporting a bumper element 45.

The embodiment also permits a modification to provide resistance to or restriction of flexion of the lumbar spine relative to the sacrum. Thus, the bone anchor 52 can be provided with a cable anchor post 54, as depicted in FIG. 11. A cable 50 may be anchored to the post 54, such as through a bore 55, using conventional cable anchoring techniques. For instance, the ends of the cable may be knotted to retain the cable within the bore, or may be looped through the bore and around the anchor post with the loop closed by a crimp.

The cable 50 may pass around the spinous process or through a hole 56 drilled through the spinous process SP of the superior vertebra, such as the L5 vertebra. The cable 50 offers no resistance to extension, since that role is fulfilled by the bumper element 45. Instead, the cable restricts flexion of the lumbar spine after a certain degree of movement as determined by the length of the cable. The cable 50 can be formed of a wound wire so that the cable acts as a positive stop to movement in flexion. Alternatively, the cable 50 may be formed of an elastic material so that the cable will stretch somewhat in flexion, thereby resisting but not preventing this movement of the spine.

Figure 33:
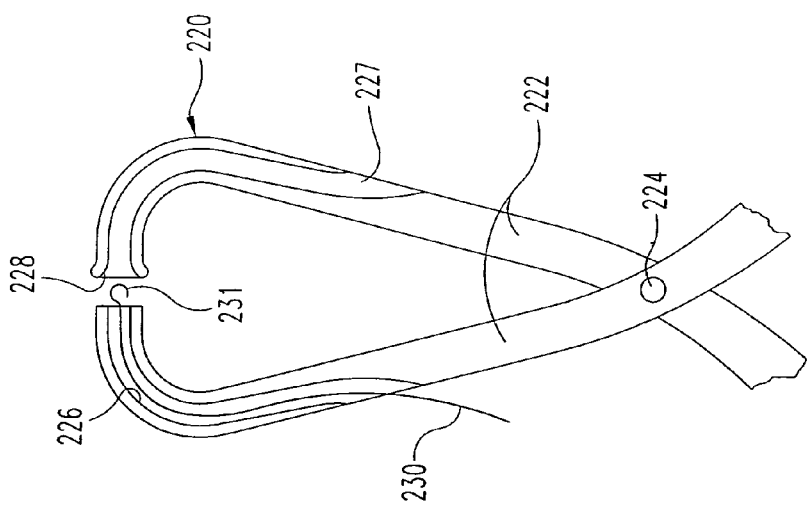
FIG. 33 is a partial view of a cable passer tool for use with certain embodiments of the bumper element of the present invention.

Passage of the flexible cable through the spinal construct is facilitated in certain embodiments by a cable passer 220, shown in FIG. 33. The cable passer 220 includes arms 222 pivotably mounted at a pivot point 224 in the configuration of a forceps instrument. The arms 222 define cable channels 226, 227 at the working end of the arms. Preferably the channels are enclosed as a passageway, but may be open in the form of a groove. The end 228 of the channel 227 may be flared to help guide the cable grabber 230 from one channel 226 to the next channel 227.

The grabber 230 may be in the form of a flexible wire that can be pushed through the two channels 226, 227. The end 231 of the grabber 230 may be in the form of a hook configured to snare an eyelet at the end of a flexible cable, for instance. The end 231 may be configured as necessary to engage the end of a cable so that the grabber 230 may be used to pull the cable back through the channels 227, 226.

Figure 34A:
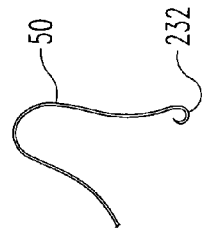
FIGS. 34a-c is a series of views of various cable configurations for use with certain embodiments of the present invention.
Figure 34B:
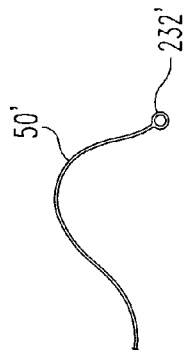
Figure 34C:
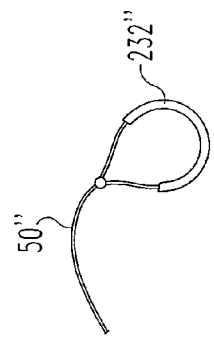

One method of using the cable passer 220 includes clamping the arms 222 of the tool about the cable opening 55 of the bolt 52 (FIG. 11). The cable passer 220 may be used with other embodiments that utilize the flexible cable, so reference to the bolt shown in FIG. 11 is only exemplary. With the arms clamped onto the bolt 52 the channels 226, 227 are aligned with the opening 55. The cable grabber 230 is then conveyed through the channel 226, through the opening 55 and into the opposite channel 227. The grabber 230 is sufficiently long so that the working end 231 exits and is accessible outside the channel 227. The flexible cable 50 may then be connected to the end 231 of the grabber, such as by engaging a hook end 232 of the cable illustrated in FIG. 34a. Examples of other cable ends 232' and 232" that can be connected to the grabber are shown in FIG. 34b-c.

Once the cable has been snagged, the grabber 230 is pulled back through the channels 226, 227 and the opening 55 until the working end 231 has exited the channel 226. The cable is then disengaged from the cable passer 220. As the tool is retracted or the arms 222 spread, the cable will fall out of the channels 226, 227 when the channels are in the form of closed passageways. When the channels 226, 227 are in the form of open grooves, the cable can be easily dislodged from the channels and the cable passer removed. The passer tool 220 may then be engaged about a second bone anchor 52 and used to grab the cable that has just been passed through the first bolt.

Alternative embodiments of the dynamic stabilizing system and bumper element of this invention are depicted in FIGS. 12-15. For example, the dynamic stabilization system 60 of FIG. 12 includes a bone screw 61 and a cap screw 63 that is engaged into a threaded bore at the top of the bone screw. The cap screw 63 may pass through a spacer 62 that is disposed or embedded within a bumper element 64. The cap screw and spacer may be complementary configured to prevent rotation of the bumper element 64 relative to the bone screw 61. It can be appreciated that the bumper element 64 may be configured in the manner of the elements 16 and 45 described above.

Figure 13:
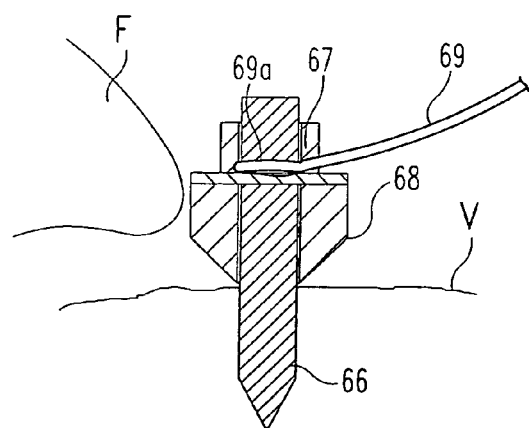
FIG. 13 is a side cross-sectional view of a dynamic stabilization system in accordance with yet another alternative embodiment of the invention.
Figure 14:
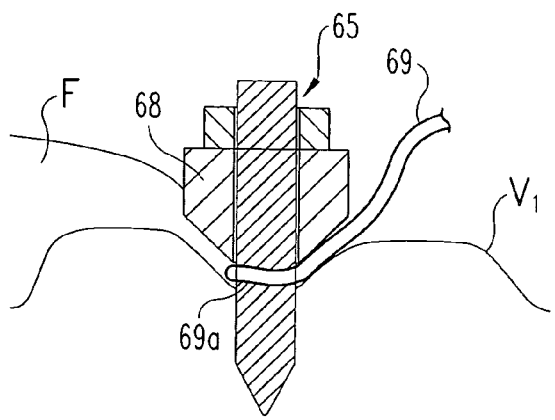
FIG. 14 is a side cross-sectional view of a dynamic stabilization system in accordance with another embodiment of the invention.
Figure 15A:
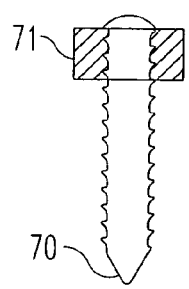
FIGS. 15a-15e include side views of several alternative embodiments of a dynamic stabilization system in accordance with the present invention.
Figure 15B:
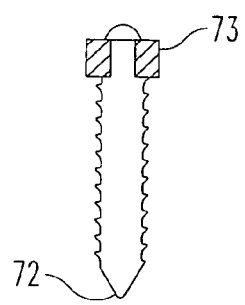
Figure 15C:
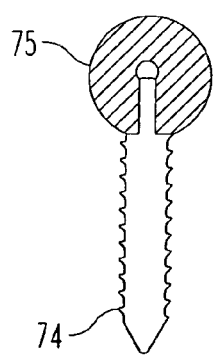
Figure 15D:
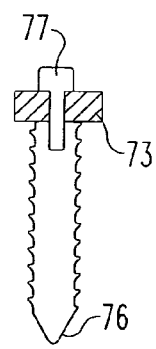
Figure 15E:
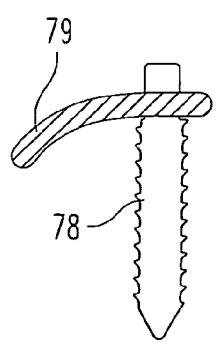

The system shown in FIG. 13 includes a conical bumper element 68 mounted over a bone anchor 66. In this embodiment, the bumper 68 bears directly against the vertebral body into which the bone anchor is implanted, while the nut 67 clamps the construct. A cable 69 can be trapped between the nut 67 and the bumper element 68. The cable 69 may then pass through or around the spinous process or other bony feature of the adjacent vertebra. As shown in FIG. 14, the cable 69 can be positioned between the bumper element 68 and the vertebra V1. In either case, the end of the cable 69 may incorporate a loop 69a through which the bone bolt or bone screw extends.

Alternative bumper element configurations are depicted in FIGS. 15a-15e. In one approach, a bone screw 70 passes through a bushing or o-ring configuration 71. A similar bushing 73 of FIG. 15b can be mounted on a bone anchor 72. The bumper element 75 shown in FIG. 15c can be in the form of a spherical ball. This bumper element 75 may include a threaded insert to permit threading the element onto a bone anchor 74. In a further alternative shown in FIG. 15d, a bone screw 76 can receive a press-fit pin 77 to clamp a bushing configuration element 73. In yet another embodiment shown in FIG. 15e, a bone anchor 78 can support a bumper element 79 that is configured to overlap the facet of the superior vertebra. With this approach, the element 79 bears against the posterior face of the facet to resist rotation of the superior vertebra V2.

As an alternative to the cable anchor post 54 of the embodiment shown in FIG. 11, an alternative embodiment of the invention contemplates a bone anchor that is modified to receive a flexible cable, such as the cable 50 shown in FIG. 10, while also supporting a bumper element, such as the element 45 in FIG. 10. Thus, as shown in FIG. 16, a bone anchor 100 includes a bone engaging portion 101, a stem 103 configured to fit within the bore of the bumper element (such as bore 34 of bumper element 16 in FIG. 4a), and a head 105. The head may be provided with driving flats 106 for engagement with a driving tool. The stem 103 and bone engaging portion 101 may be configured as the like components of the bone anchor 12 shown in FIG. 4a.

However, unlike that prior bone anchor, the bone anchor 100 incorporates features that are adapted to receive a flexible cable to form a construct such as the construct shown in FIG. 10. More specifically, the head 105 defines a plurality of holes 107 that pass through the head. Preferably, each hole 107 intersects opposite flats 106 so that in the illustrated embodiment three such holes are provided to receive the cable. With this configuration, the head 105 may be rotated until one of the plurality of holes is properly aligned to accept a cable.

As can be seen in the embodiment of FIG. 16, the bolt 100 includes a head 105 that is larger than the bore (34) in the bumper element (16). Thus, no nut is required to clamp the bumper element in position. With this embodiment, the bumper element is clamped underneath the enlarged head 105 and against the surface of the vertebra, like the embodiments shown in FIGS. 13-14.

In a further alternative, a specially configured nut may be provided with features for engaging a flexible cable, such as cable 50. As shown in FIGS. 17*a-c*, a nut 110 may be configured with internal threads 112 for engagement with the machine threads of a bone bolt, such as threads 25 of the bolt 12 shown in FIG. 4*a*. In addition, the upper portion of the nut may define at least one hole 114 therethrough. The hole 114 is configured to receive a cable therethrough to form a construct such as the construct shown in FIG. 10. Alternatively, a plurality of holes may be provided through each pair of opposite driving flats.

Figure 18:
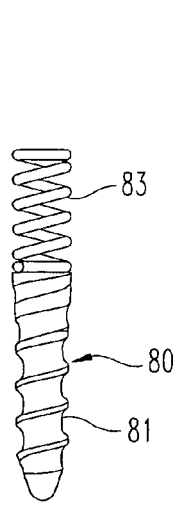
FIG. 18 is a side view of another embodiment of a dynamic stabilization system of the present invention.
Figure 19A:
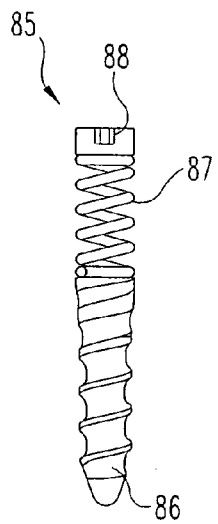
FIG. 19a is a side view of a further embodiment of a dynamic stabilization system of this invention incorporating a spring.
Figure 19B:
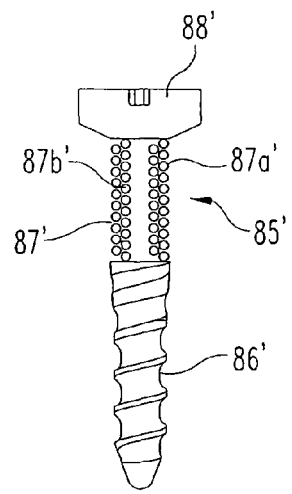
FIG. 19b is a side view of another embodiment of the invention incorporating a spring
Figure 20:
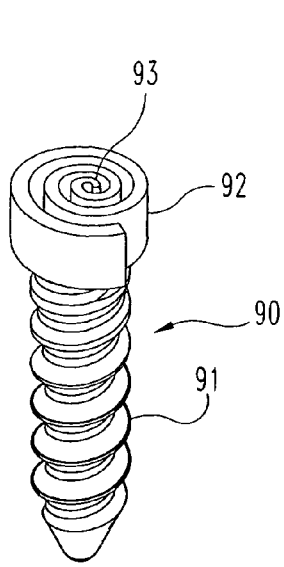
FIG. 20 is a side view of yet another dynamic stabilization system of the invention that incorporates a torsion spring.

The present invention further contemplates a dynamic stabilization system in which the dynamic resistive element is incorporated into the bone engaging fastener, as shown in FIGS. 18-20. For instance, the dynamic stabilization element 80 shown in FIG. 18 includes a bone engaging portion 81 and a deflectable portion 83. In one embodiment, the deflectable portion 83 is in the form of a helical coil spring, preferably tightly wound to provide ample strength for distraction of the adjacent vertebra. The spring portion 83 may be integrally formed with the bone engaging portion 81 or may be permanently affixed in a suitable manner.

In an alternative approach, a dynamic stabilization element 85 includes a deflectable portion 87 fixed to a bone screw 86 by a cap 88, as shown in FIG. 19*a*. The deflectable portion 87 may be in the form of a torsion screw that can be adjusted to adjust the bending resistance of the portion. Rotation of the cap 88 rotates the torsion screw to tighten or loosen the deflectable portion.

In a modification shown in FIG. 19*b*, the deflectable portion 87' of an element 85' includes concentric springs 87*a'* and 87*b'* wound counter to each other. The cap 88' may be enlarged to overlap the facet F to prevent the facet from shifting over the cap 88' during certain movements of the spine.

The dynamic stabilization element 90 shown in FIG. 20 contemplates replacing the spring of the version in FIG. 18 with a leaf spring 92 mounted to a bone screw 91. The leaf spring 92 may be of a variety of configurations, although a preferred configuration is in the form of a loosely wound band coil. With this embodiment, the leaf spring 92 compresses rather than bends. The inner edge 93 of the leaf spring may be fixed within a slot (not shown) at the upper end of the bone screw 91. The element 90 may be provided with a cap (not shown) that fits over the top of the leaf spring to retain the spring on the screw, and/or to provide a deflection limit for the element.

Figure 21A:
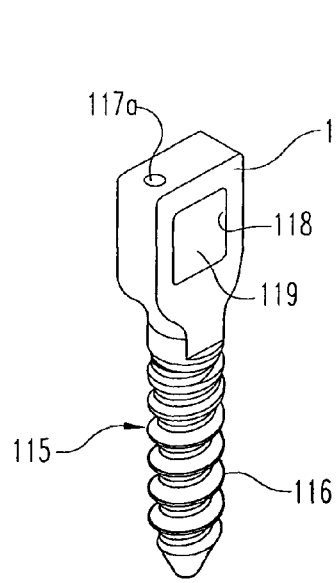
FIG. 21a is a perspective view of an additional dynamic stabilization system of the invention incorporating an expandable balloon element, with the element in its contracted configuration.
Figure 21B:
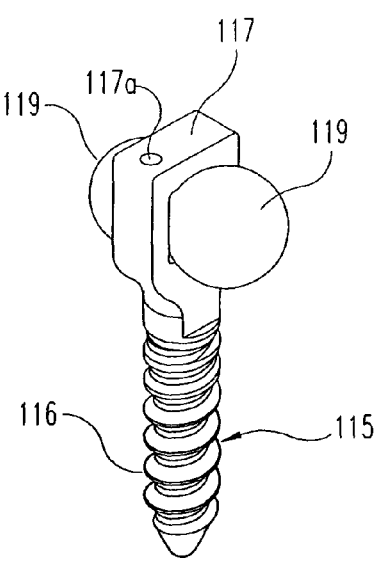
FIG. 21b is a perspective view of the dynamic stabilization system shown in FIG. 21a, with the balloon element in its expanded configuration.

In the embodiments described above, the bumper element or spring elements have a fixed configuration that must be accommodated during implantation within the spine. In an alternative approach, the bumper element may have a first smaller configuration for percutaneous introduction and a larger expanded configuration for performing the dynamic stabilization function. Thus, as shown in FIGS. 21*a*-21*b*, a stabilization element 115 may include a bone screw 116 configured for engagement in a vertebral body. The head portion 117 of the element may define a cavity 118 which houses an expandable element 119.

The expandable element 119 may be a balloon that has a smaller configuration sized to retain the balloon within the cavity. As shown in FIG. 21*b*, the balloon expandable element 119 has a larger expanded configuration that is sized so that the balloon can bear against exterior features of an adjacent vertebra. In the embodiment illustrated in FIG. 21*b*, the expandable element projects from opposite sides of the head portion 117, although the balloon and cavity 118 may be configured so that the balloon expands in one direction only. In this embodiment, the expandable element 119 or balloon may have a predefined expanded configuration. The head portion 117 may incorporate a valve element 117*a* that provides access for an inflation needle. The expandable element 119 is preferably expanded by pressurized introduction of saline into the element.

In the embodiment shown in FIGS. 22*a*-22*b*, the stabilization element 115' includes a bone screw portion 116' and a head portion 117' similar to the stabilization element 115. In this embodiment, the head portion 117' defines a cavity 118' that opens at the top of the head portion, rather than at the sides. The expandable element 119' resides initially entirely within the cavity 118'. Upon expansion, the expandable element or balloon extends above the head portion 117', as depicted in FIG. 22*b*. Again, the expandable element may have a predetermined expanded configuration to bear on appropriate features of the adjacent vertebrae.

In certain previous embodiments, a cable or wire may be incorporated into the dynamic stabilization system to resist or prevent flexion. Alternative cable approaches are illustrated in FIG. 23*a-b*. In one embodiment, the dynamic stabilizer 10 shown in FIG. 3 includes a cable 94 engaged to the bone anchor 12 or bumper element 16. The cable 94 may reside within the groove 33 (FIG. 5) on the edge opposite the contoured edge 33 of the bumper element 16. As shown in FIG. 23*a*, the cable 94 passes around or through the spinous process SP of the superior vertebra. The cable variably resists flexion of the vertebrae as the dynamic stabilization system 10 deflects when the cable is placed in tension. As shown in FIG. 23*b*, the cable may instead be wound around the flats 27 of the bone anchor 12 supporting the bumper element 16. These flats may also be engaged by the bumper element.

Figure 24A:
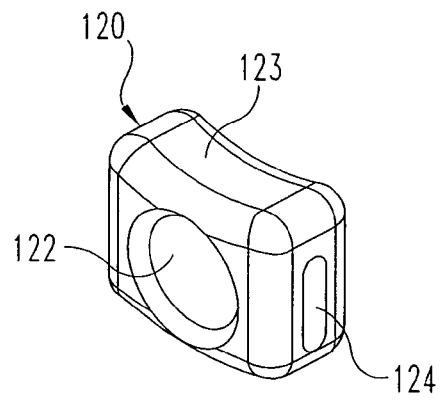
FIG. 24a is a perspective view of an alternative embodiment of a bumper element for a dynamic stabilization system of the present invention.
Figure 24B:
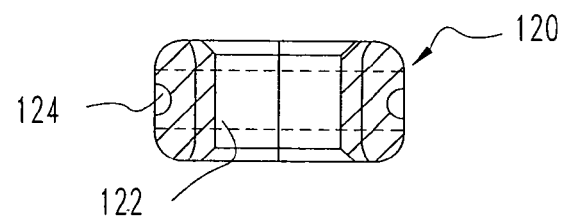

In the prior embodiments, one preferred material for the bumper element is an elastomeric material, such as silicone or polyurethane. In optional embodiments, the bumper element may be formed of a biocompatible metal, such as titanium or stainless steel. One such bumper element 120 is depicted in FIG. 24. The bumper element 120 defines a bore 122 adapted to reside around the stem of a bone bolt, such as the stem 23 of bolt 12 (FIG. 4*a*) or the stem 103 of bolt 100 (FIG. 16). The contour of the element may define a curved surface 123 that approximates the contoured surface 49 of the bumper element 45 (FIG. 9*a*) for engagement with the facet of an adjacent vertebra. The side walls of the bumper element preferably define engagement recesses 124 that are configured for engagement with mating protrusions on an insertion tool. The recesses allow the bumper element to be gripped by the insertion tool for positioning adjacent the spine.

Figure 32A:
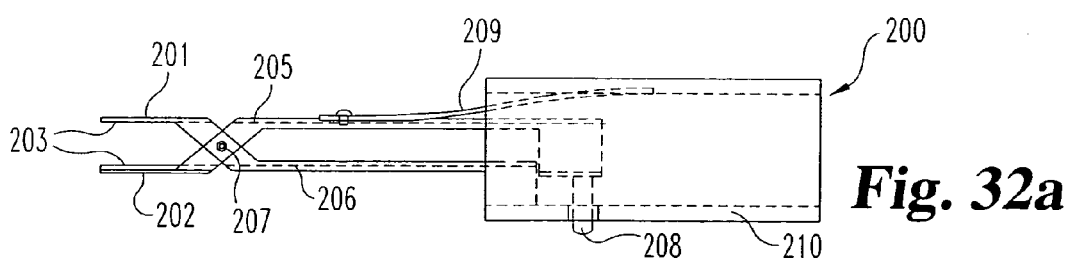
FIG. 32a is a side view of a bumper inserter tool according to one embodiment of the invention.
Figure 32B:
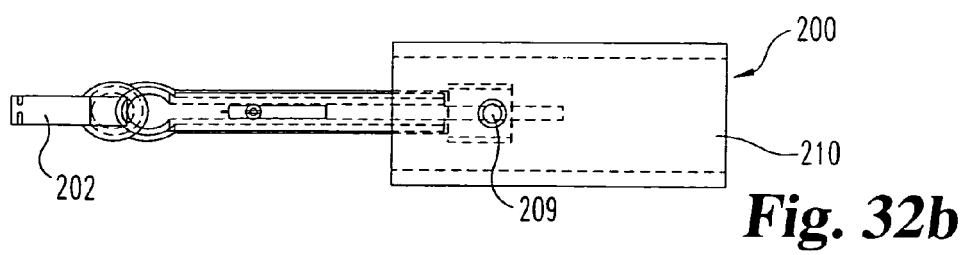

One embodiment of an inserter adapted for engaging the recesses 124 is illustrated in FIGS. 32*a*-32*b*. The inserter 200 includes a pair of engagement arms 201, 202, each terminating in a projection 203 adapted to fit snugly within the engagement recesses 124. The arms are integral with a corresponding fixed fulcrum 206 and a movable fulcrum 205 that are rotatably connected at a pivot point 207. The fixed fulcrum is engaged to or integral with a handle 210. The movable fulcrum 205 includes a leaf spring 209 engaged between the fulcrum 205 and the handle 210 so that the movable fulcrum is biased to an engagement position in which the projections 203 are disposed within the recesses 124 of the bumper element 120.

The movable fulcrum may include a release button 208 that is depressed relative to the handle 210 and against the operation of the leaf spring 209 to pivot the arm 202 relative to the opposite arm 201. This movement of the arm 202 releases the arms 201, 202 from the bumper element. The travel of the button 208 is limited so that the arm 202 pivots only as much as is necessary to disengage the bumper element.

The bumper element 120 of FIG. 24 is less resilient than the embodiments discussed above, and is preferably used where a substantially rigid structure between adjacent vertebrae is desired. It should be understood that even with a generally rigid bumper element, such as element 120, the element only restrains movement of the adjacent vertebrae toward each other (i.e., in extension), and not movement apart (i.e., in flexion).

Alternative flexible bumper elements are depicted in FIGS. 25-30 in which the flexibility is more a function of the structure of the element rather than the material. The bumper elements of these embodiments may be formed of any biocompatible material, including the elastomeric materials discussed above. The structures of these elements are also well-suited to being formed of a non-elastomeric material, such as a metal.

Figure 25A:
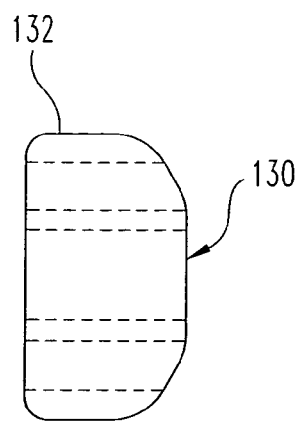
FIG. 25a is a side view of a bumper element formed of a non-resilient material or metal in accordance with a further embodiment of the invention.
Figure 25B:
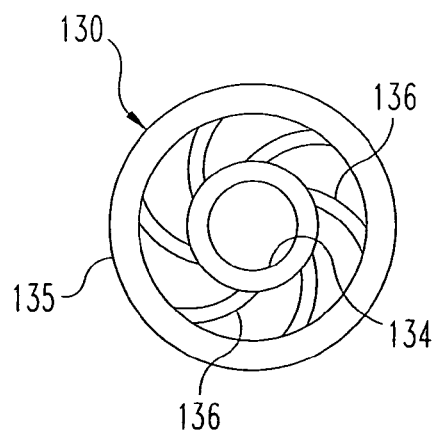

Referring first to FIGS. 25a-25b, a flexible bumper element 130 defines an outer surface 132 that is contoured to mate with an articulating element of an adjacent vertebra, such as the facet. The element includes a central ring 134 and an outer ring 135 which defines the contoured surface 132. The central ring 134 defines an opening through which a bone anchor, such as the bolt 12, may pass to engage the bumper element to a vertebra.

The two rings are connected by a series of spring elements 136 that are preferably in the form of webs arranged in a semi-spiral configuration, as depicted in FIG. 25b. In one specific embodiment, the central and outer rings 134 and 135 are substantially rigid. The deformation of the bumper element 130 is accomplished by flexing of the spring elements 136 as the outer ring 135 is pushed toward the central ring 134. The spiral arrangement of the webs allows the webs nearest the point of engagement with the adjacent vertebra to collapse against the central ring 134, while the webs opposite this point expand as the outer ring 135 moves away from the central ring. The stiffness of the bumper element 130 may be adjusted by controlling the thickness of the spring elements 136. The diameter of the outer ring 135 may also be adjusted to accommodate the anatomy of the instrumented vertebral level.

Figure 26:
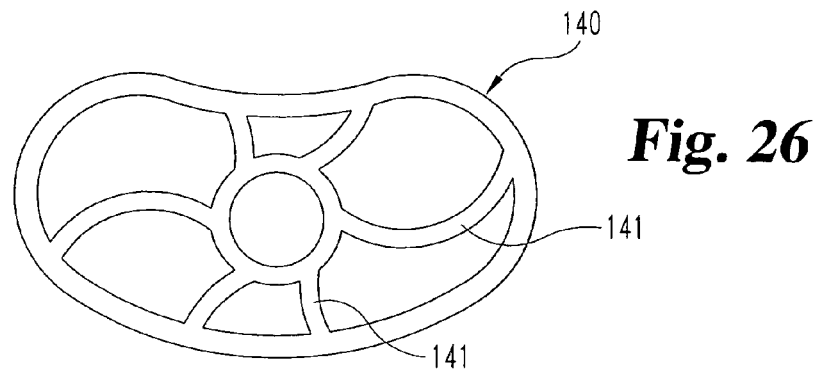
FIGS. 26-30 depict flexible bumper elements preferably formed of a non-resilient material or a metal in accordance with alternative embodiments of the invention.
Figure 27:
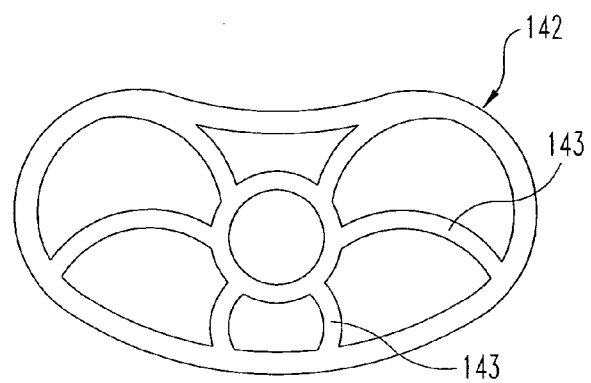
Figure 28:
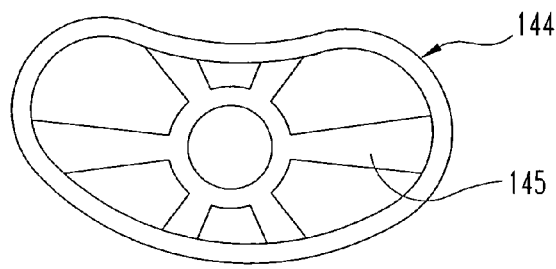
Figure 29:
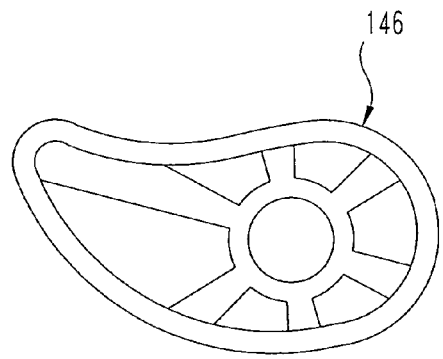

This same concept may be implemented with different external and internal geometries. Thus, kidney shaped bumper elements 140, 142 and 144 may be configured as shown in FIGS. 26-28. As can be seen in the figures, the respective spring elements 141, 143 and 145 are not uniform throughout the entire bumper elements 140, 141. The bumper element 146 shown in FIG. 29 adopts the cam configuration adopted in connection with the resilient bumper element 10 shown in FIG. 3.

Figure 30:
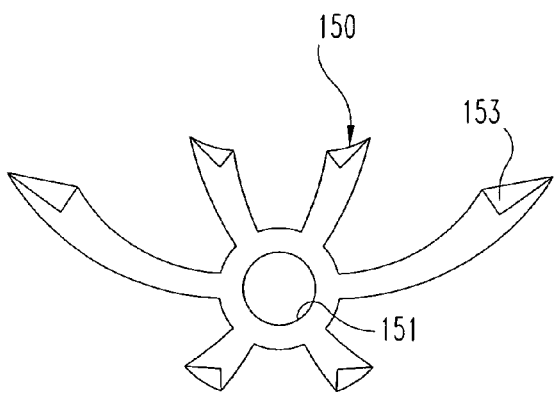

The bumper element 150 shown in FIG. 30 is similar to the bumper element 144 of FIG. 28, except that the outer ring has been removed. Thus, the element 150 includes a central ring 151 configured for engagement with a bone anchor, and a plurality of spring elements 153 emanating from the ring. The spring elements may be arranged and sized to offer the same resistance as the spring elements in any of the embodiments shown in FIGS. 25-29.

Figure 31A:
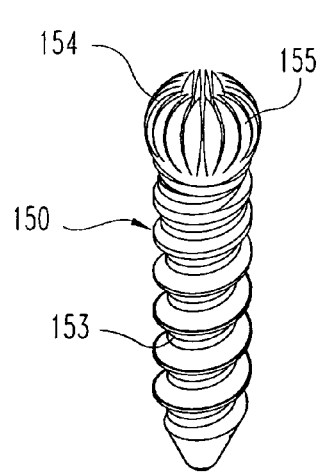
FIGS. 31a, b are perspective views of an alternative flexible bumper element.
Figure 31B:
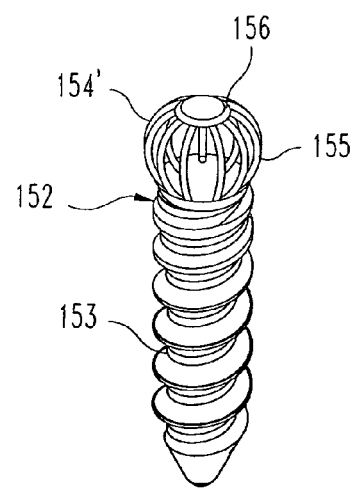

A related approach may be implemented at the head of a bone bolt. Thus, as shown in FIGS. 31a-b, a bone anchor 150 or 152 includes a bone engaging portion 153 and a head portion 154. The head portion 154 may be in the form of a plurality of spring elements 155 projecting upward from the bone engaging portion. The spring elements 155 may be free at their ends, as shown in FIG. 31a, or may include a central ring 156, as shown in FIG. 31b. The principle of operation of the head portions 154, 154' of the bone anchors 150 and 152 is similar to the embodiments shown in FIGS. 25-30.

Figure 35:
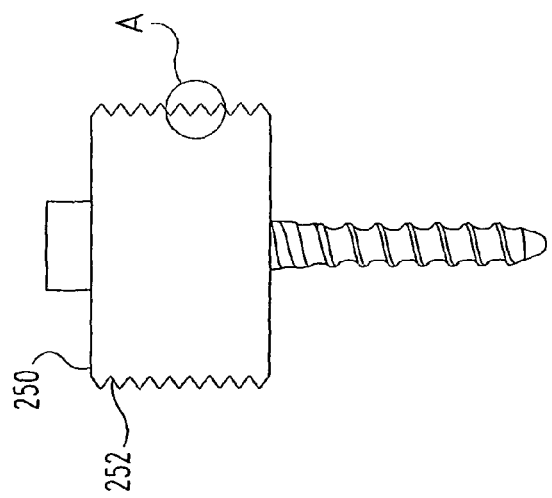
FIG. 35 is a side view of a flexible bumper element in accordance with yet another embodiment of the invention.

In order to improve the contact between the bumper element and the vertebral body, a bumper element 250 shown in FIG. 35 may be provided with a surface feature 252 that encourages a fuller contact area with the bone. The bumper element 250 may be configured like any of the bumper elements described above. As shown in the detail views of FIGS. 36a, b, the surface feature 252 may include teeth 254 or truncated teeth 256 that contact the facet, for instance. The surface feature 252 may be deformable and resilient so that the teeth deform upon contact with the vertebral bone to increase the surface area of contact.

Figure 36B:
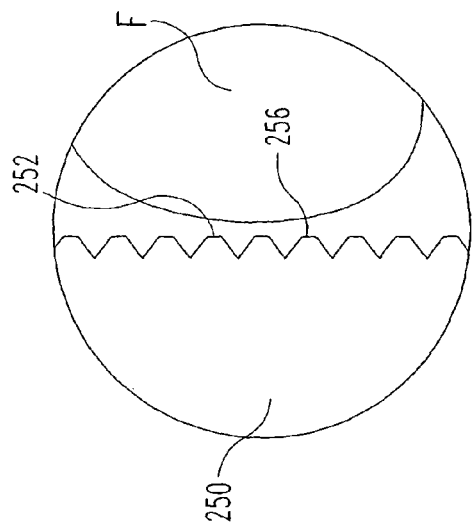
FIGS. 36a, b are enlarged views of the portion A of the bumper element of FIG. 35, shown with different surface configurations for the bumper element.
Figure 36A:
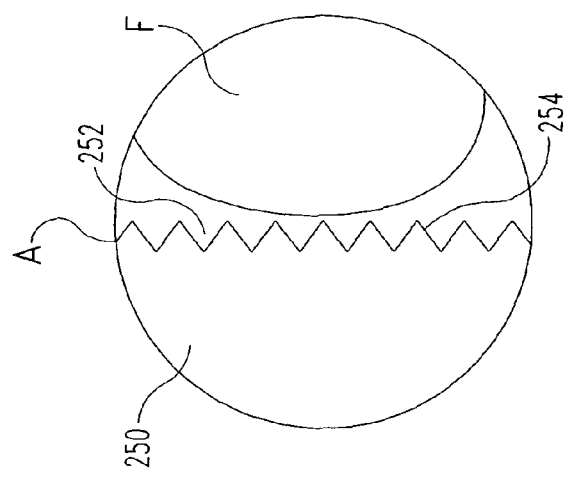
Figure 37:
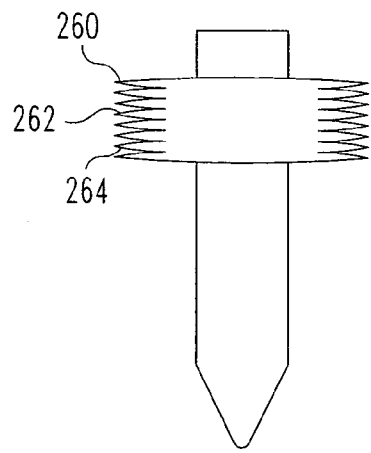
FIG. 37 is a side view of a flexible bumper element according to still another embodiment of the invention.
Figure 38:
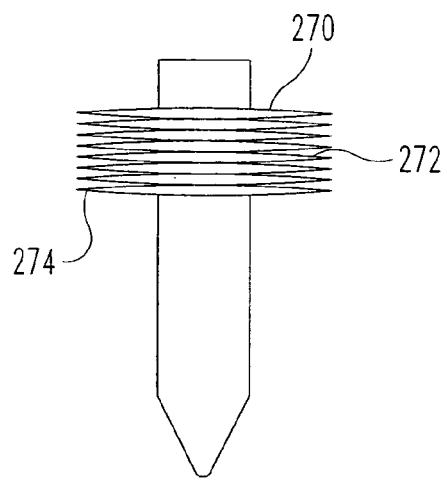
FIG. 38 is a side view of a flexible bumper element utilizing a stack of flexible wafers in accordance with another embodiment of the invention.

In the embodiments shown in FIGS. 37-38, the respective bumper elements 260, 270 include respective surface features 262, 272 that permit greater deformation than the surface features 252 in the embodiments of FIGS. 36a-36b. The surface feature 262 includes generally triangular teeth 264 that are similar to the teeth shown in FIG. 36a except thinner and deeper. The teeth 264 can deflect under pressure from the facet, with adjacent teeth deflecting into contact to gradually increase the resistance against the facet movement.

The surface feature 272 for the bumper element 270 of FIG. 38 is similar to the feature 262 except that the teeth are formed by one or more wafers 274. In one preferred embodiment, each tooth row constitutes a single wafer. A nut threaded onto the mounting screw will compress the wafers 274 into a uniform stack.

Figure 39:
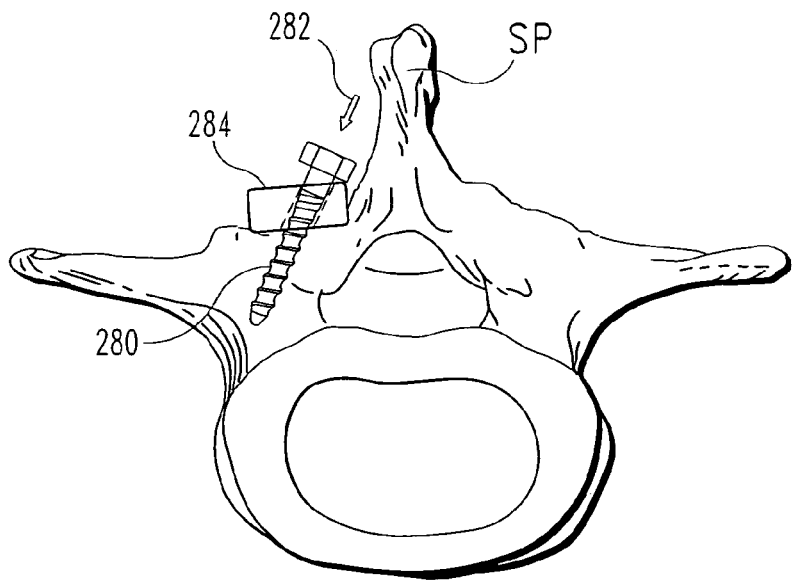
FIG. 39 is an A-P view of a vertebra showing a surgical approach for engaging a flexible bumper element to the vertebral body according to one embodiment of the invention.
Figure 41:
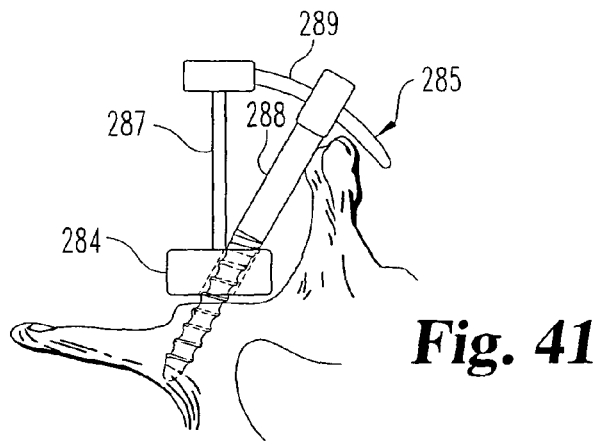
FIG. 41 is a partial A-P view of a jig for use in performing the alternative approach shown in FIG. 39.

In one procedure for implanting one of the bumper elements described above, the vertebral body may be accessed from the lateral side of the vertebral body to which the bumper element is to be engaged. In an alternative approach, depicted in FIGS. 39 and 41, a bumper element screw 280 may be implanted from the contralateral side. Although the trajectory 282 of the screw 280 may be through an opening in the spinous process, preferably the trajectory includes a superior or inferior component so that the screw need not pass through the spinous process.

A jig 285 may be used to guide the implantation of the bumper element screw 280. The jig 285 may include a guide element 287 that indexes off the bumper element 284 when it is situated on the vertebral body in its desired position. A screw guide 288 is moved along a guide track 289 until the proper trajectory is obtained. This trajectory may be directly visualized or may be discerned with the aid of an imaging device.

Figure 40A:
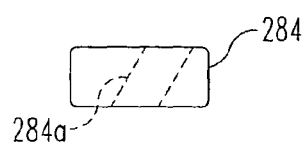
FIGS. 40a, b are side and top views of a flexible bumper element modified for engagement to the vertebral body using the alternative approach shown in FIG. 39.
Figure 40B:
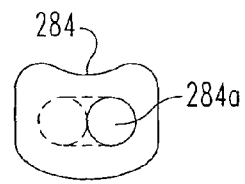

In order to accommodate the contralateral screw fixation, the bumper element 284 may include a screw hole 284a that is aligned at an angle relative to the bumper element, as shown in FIGS. 40a-40b. The angle of the screw hole dictates, at least in part, the screw trajectory. In one method, the screw guide 288 engages the screw hole 284a to establish the trajectory. The guide is then fixed to the guide track and the screw threaded into the bone.

Figure 42:
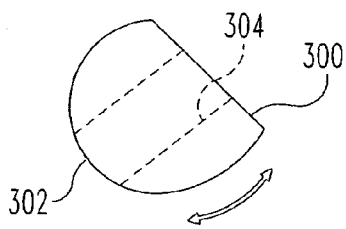
FIG. 42 is a side view of a rounded bumper element according to an embodiment of the invention.
Figure 43:
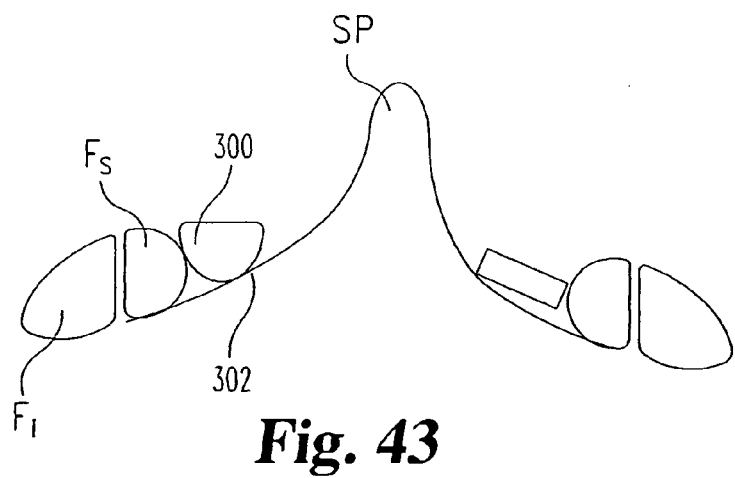
FIG. 43 is a partial A-P view of a spinal motion segment with the bumper element shown in FIG. 42.

In a further embodiment, a bumper element 300 is provided with a rounded bone engaging surface 302, as shown in FIGS. 42-43. The screw bore 304 passes through the element 300 and accepts a bone fixation screw in the manner described above with respect to the prior embodiments. The curved or rounded surface allows the bumper 300 to sit more stably between the superior facet Fs and the vertebral body to which it is engaged, as shown in FIG. 43. This rounded bone engaging surface may be incorporated into the bumper elements described above.

The present invention contemplates a system capable of providing intervertebral distraction without immobilization or fusion. The dynamic stabilization system of this invention resists or restricts bending of the spine in one direction but not the opposite—i.e., resists bending in extension but not flexion. In the preferred embodiments, the systems include bumper elements configured to engage the facet of a superior vertebra. Moreover, the systems contemplate engagement to the inferior vertebral body, such as at the pedicles or laminae.

It is further contemplated that the dynamic stabilization systems of the present invention may be provided as a kit of parts. In one embodiment the kit of parts may include at least a pair of first bone fasteners configured for anchoring in a vertebra, at least a pair of second bone fasteners configured for anchoring in the sacrum, and at least a pair of deflectable elements adapted to be selectively supported on either the first pair of bone fasteners or the second pair of bone fasteners. The deflectable elements are adapted to contact a portion of a superior vertebra when supported by the selected fasteners. In other embodiments, the kit of parts can further include a cable adapted to be selectively connected to either the first pair of bone fasteners or said the pair of bone fasteners. The cable has a length to extend around the spinous process of the superior vertebra when the cable is connected to the selected fasteners.

The dynamic stabilization systems of the present invention maintain distraction of the instrumented vertebral level, thereby helping to relieve pain symptoms associated with foraminal stenosis, central soft stenosis or facet pain. The systems can be calibrated to induce a slight kyphosis or to simply restrict movement in extension. In certain embodiments, the dynamic stabilization system may include a cable that engages the superior vertebra to resist hyper-flexion of the vertebrae.

In all of the embodiments, the dynamic stabilization systems are most preferably capable of implantation using minimally invasive surgical techniques. These systems are particularly suited for posterior procedures using known working channel technology.

It is contemplated that the dynamic stabilization system of the present invention may be used at any number of spinal levels. For instance, the construct shown in FIG. 10 may include the sacral and cable fixation between the S1 and L5 vertebrae depicted in that figure, together with a construct like that shown in FIG. 3 between the L5 and L4 vertebrae. Alternatively, the anchor and cable construct shown in FIG. 10, or the deflectable element arrangement of FIG. 3, may be implemented at several vertebral levels.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A dynamic stabilization system for the spine comprising:
   a pair of elongate bone engaging fasteners each having a transverse profile of a first transverse extent and each configured to be anchored in an inferior vertebra on opposite sides of the spinous process of the vertebra; and
   a deflectable element that is resiliently deformable mounted on each fastener, each of said deflectable elements defining a second transverse extent greater than said first transverse extent, and each of said deflectable elements being sized and arranged on a respective fastener to contact, along a portion of said second transverse extent, a lower portion of an adjacent superior vertebra during extension of the spine when said pair of fasteners is engaged within a vertebra.

2. The dynamic stabilization system of claim 1, further comprising a cable connected at its ends to a corresponding one of said pair of bone engaging fasteners, said cable sized to engage a portion of the adjacent vertebra.

3. The dynamic stabilization system of claim 2, wherein said deflectable element is configured and arranged to contact the facet of the adjacent vertebra.

4. The dynamic stabilization system of claim 2, wherein said cable is sized to engage the spinous process of the adjacent vertebra.

5. The dynamic stabilization system of claim 2, wherein:
   each of said bone engaging fasteners includes a post defining a bore sized to receive said cable therethrough; and
   said ends of said cable are configured to pass through said bore in each of said bone engaging fasteners.

6. The dynamic stabilization system of claim 2, wherein:
   each of said bone engaging fasteners includes;
   a shank having bone engaging threads;
   a threaded stem; and
   a nut configured to engage the threaded stem, said nut defining a bore for passage of said cable therethrough; and
   said deflectable element defines an opening to receive said threaded stem therethrough, whereby said nut bears on said deflectable element to mount said deflectable element on said fastener.

* * * * *